(12) United States Patent
Nagamizu et al.

(10) Patent No.: US 8,913,112 B2
(45) Date of Patent: Dec. 16, 2014

(54) IMAGE PICKUP UNIT FOR ENDOSCOPE (75) Inventors: Hiroyuki Nagamizu, Sagamihara (JP); Koichi Shiotani, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 70 days.

(21) Appl. No.: 13/560,391

(22) Filed: Jul. 27, 2012

(65) Prior Publication Data

US 2012/0293641 A1 Nov. 22, 2012

Related U.S. Application Data

(63) Continuation of application No. PCT/JP2010/067952, filed on Oct. 13, 2010.

(30) Foreign Application Priority Data

Feb. 1, 2010 (JP) ................................. 2010-020496

(51) Int. Cl.
*A62B 1/04* (2006.01)
*A61B 1/04* (2006.01)
*A61B 1/06* (2006.01)
*H04N 9/47* (2006.01)
*H04N 7/18* (2006.01)
*A61B 1/00* (2006.01)
*G02B 23/24* (2006.01)
*A61B 1/05* (2006.01)

(52) U.S. Cl.
CPC ........ *A61B 1/00163* (2013.01); *G02B 23/2484* (2013.01); *A61B 1/00096* (2013.01); *A61B 1/05* (2013.01)
USPC .......................................................... 348/65

(58) Field of Classification Search
None
See application file for complete search history.

(56) References Cited

U.S. PATENT DOCUMENTS

| | | | |
|---|---|---|---|
| 5,569,162 A | 10/1996 | Komi | |
| 6,704,052 B1* | 3/2004 | Togino et al. | 348/340 |
| 2003/0233024 A1* | 12/2003 | Ando | 600/111 |
| 2007/0046778 A1* | 3/2007 | Ishihara et al. | 348/68 |
| 2009/0073261 A1* | 3/2009 | Takemura et al. | 348/71 |
| 2009/0268019 A1* | 10/2009 | Ishii et al. | 348/65 |
| 2011/0069162 A1* | 3/2011 | Ozawa et al. | 348/68 |

FOREIGN PATENT DOCUMENTS

| | | |
|---|---|---|
| CN | 101404922 A | 4/2009 |
| JP | 04-235477 | 8/1992 |
| JP | 5-9504 | 2/1993 |
| JP | 06-070882 | 3/1994 |

(Continued)

OTHER PUBLICATIONS

International Search Report dated Nov. 30, 2010.

*Primary Examiner* — Joseph Ustaris
*Assistant Examiner* — Kevin McInnish
(74) *Attorney, Agent, or Firm* — Scully, Scott, Murphy & Presser, P.C.

(57) ABSTRACT

An image pickup unit includes a dioptric system that reflects a luminous flux of an optical image incident on an optical lens group and performs optical path conversion, an image sensor in a bare state that is joined to the dioptric system, and includes a light receiving element that forms the optical image, and a light shielding member that is placed to be opposed to and cover at least surfaces around an optical axis of the optical lens group, except for a joining surface of the dioptric system to the image sensor, so that an air gap apart from the image sensor by a predetermined distance is provided, shields incidence of a harmful light onto the light receiving element, and is formed from a metal thin film.

9 Claims, 12 Drawing Sheets

(56) References Cited

FOREIGN PATENT DOCUMENTS

| JP | 08-000552 | 1/1996 |
| JP | 08-076028 | 3/1996 |
| JP | 11-249030 | 9/1999 |
| JP | 2001-128930 | 5/2001 |
| JP | 2007-052358 | 3/2007 |
| JP | 2009-058807 | 3/2009 |

* cited by examiner

FIG.13

IMAGE PICKUP UNIT FOR ENDOSCOPE

CROSS REFERENCE TO RELATED APPLICATION

This application is a continuation application of PCT/JP2010/067952 filed on Oct. 13, 2010 and claims benefit of Japanese Application No. 2010-020496 filed in Japan on Feb. 1, 2010, the entire contents of which are incorporated herein by this reference.

BACKGROUND OF THE INVENTION

1. Field of the Invention

The present invention particularly relates to an image pickup unit for an endoscope which is contained in a distal end portion, in image pickup units for endoscopes provided in electronic endoscope apparatuses.

2. Description of the Related Art

In recent years, endoscopes have been widely utilized in a medical field and an industrial field. In conventional endoscopes, image guides have been used, and endoscopes which enable users to observe insides of body cavities of patients, inner portions of jet engines or the like in eyepiece portions which users look into have been typical.

Further, in recent endoscopes, an electronic endoscope apparatus has appeared, in which an image pickup unit provided with a solid image pickup device is incorporated in a distal end portion of an insertion portion, photographs the inside of the body cavity of a patient, the inner portion of a jet engine or the like, and displays an endoscopic image on a display apparatus such as an external monitor.

The image pickup unit of the electronic endoscope apparatus is provided with an image sensor which photoelectrically converts detected light into an electric signal. As the image sensor, the image sensor with a solid image pickup device, an electronic circuit and the like being packaged as one electronic component has been typical.

Further, the image pickup unit for use in an electronic endoscope is required to have such a size as to be capable of being housed inside of a downsized distal end portion with reduction in a diameter of an insertion portion. Therefore, some of the image pickup units placed in the distal end portions of endoscope apparatuses with small housing spaces use prisms as structures which cause refracted lights to be incident on image sensors, in order to prevent the distal end portions from being upsized in an outside diameter direction in particular.

For example, Japanese Utility Model Application Laid-Open Publication No. 5-9504 discloses a technology of a solid image pickup device package that has a holding member which holds a barrel and a prism which are integrated, and completely prevents separation of a cover glass and a package body made of ceramics by the holding member. In the solid image pickup device package described in the Japanese Utility Model Application Laid-Open Publication No. 5-9504, the package body of ceramics, and the holding member formed from a metal material or a synthetic resin material are used.

Incidentally, light shielding ability for unnecessary light to a light receiving element is required for an image pickup unit so that a light other than a photographing optical image is not detected in the light receiving element of the solid image pickup device.

SUMMARY OF THE INVENTION

An image pickup unit for an endoscope of an aspect of the present invention includes a dioptric system that reflects a luminous flux of an optical image incident on an optical lens group and performs optical path conversion, an image sensor in a bare state that is joined to the dioptric system, and includes a light receiving element on which the luminous flux is incident and forms the optical image, and a light shielding member that is placed to be opposed to and cover at least surfaces around an optical axis of the optical lens group, except for a joining surface of the dioptric system to the image sensor so that an air gap apart from the image sensor by a predetermined distance is provided, shields incidence of a harmful light onto the light receiving element, and is formed from a metal thin film.

An image pickup unit for an endoscope of another aspect of the present invention includes a bending optical system that reflects a luminous flux of an optical image incident on an optical lens group and performs optical path conversion, an image sensor in a bare state that is joined to the bending optical system, and includes a light receiving element on which the luminous flux is incident and forms the optical image, and a light shielding member that is placed to be opposed to and cover surfaces around an optical axis of the optical lens group in the bending optical system so that an air gap apart from the bending optical system by a predetermined distance is provided, shields incidence of a harmful light onto the light receiving element, and is formed from a metal thin film.

DETAILED DESCRIPTION OF THE PREFERRED EMBODIMENTS

Hereinafter, an image pickup unit which is the present invention will be described. It should be noted that in the following description, the drawings based on respective embodiments are only schematic, and the relationship of the thickness and the width of each portion, the ratios of thickness of respective portions and the like differ from the actual ratios, and portions where the mutual size relationships and ratios differ among the drawings may be included.

First Embodiment

Figure 1:
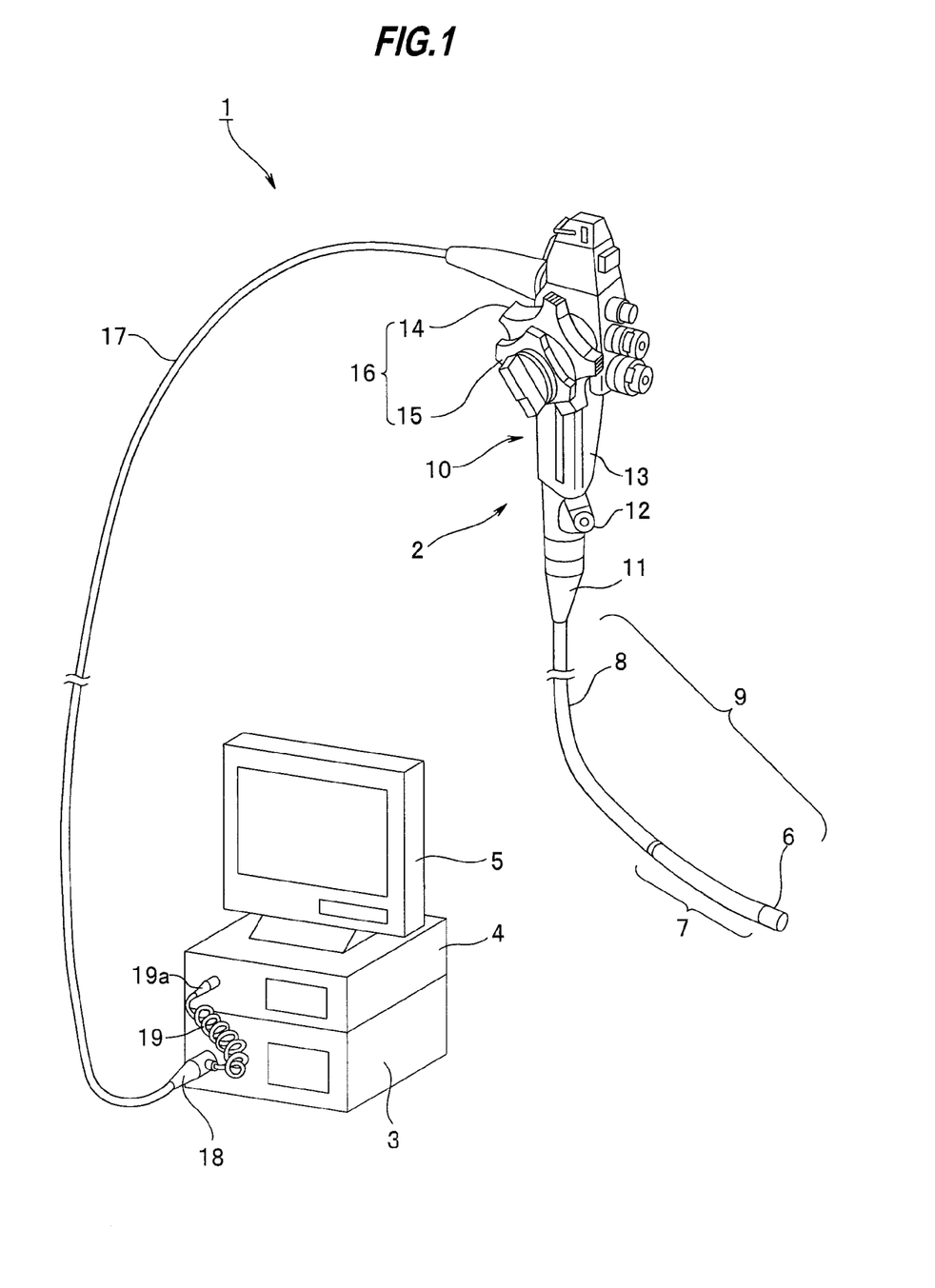
FIG. 1 relates to a first embodiment of the present invention, and is a view showing an electronic endoscope system including an electronic endoscope apparatus.
Figure 2:
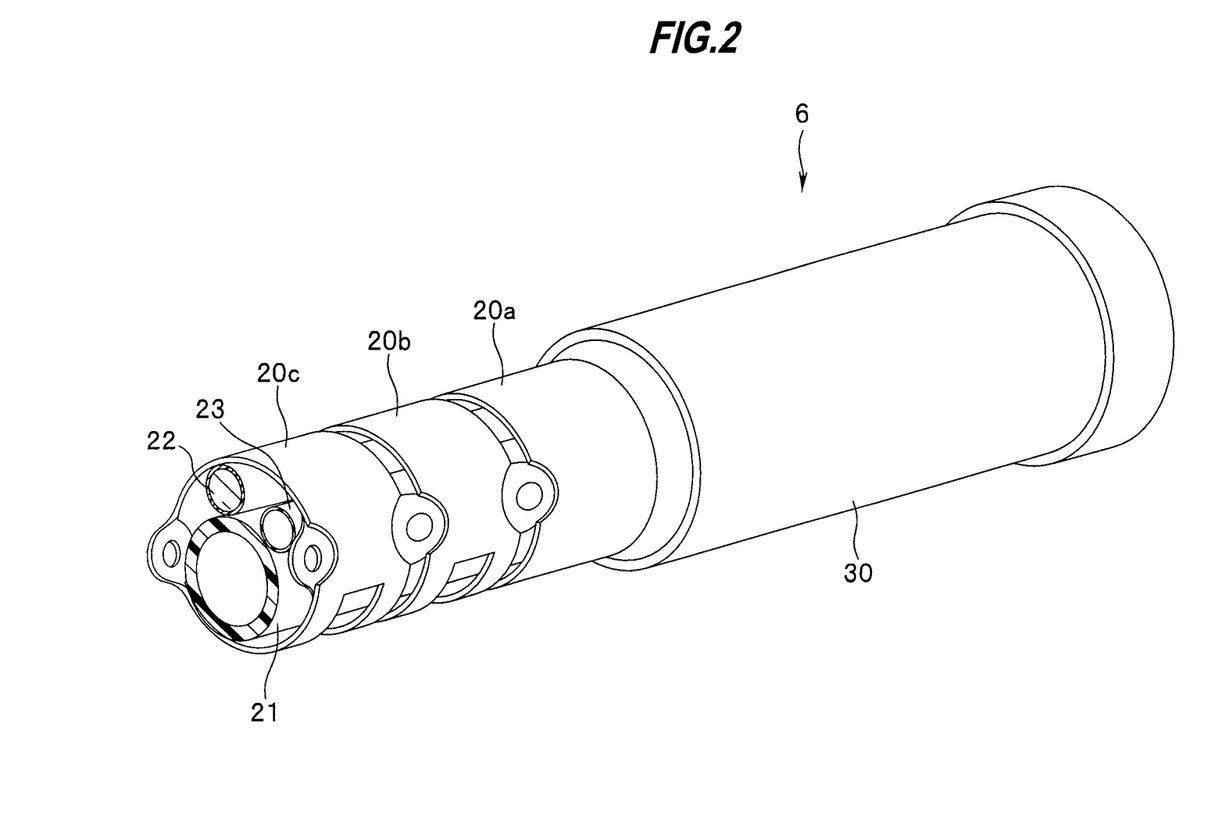
FIG. 2 relates to the first embodiment of the present invention, and is a perspective view showing an inner portion of a distal end portion of an insertion portion.
Figure 3:
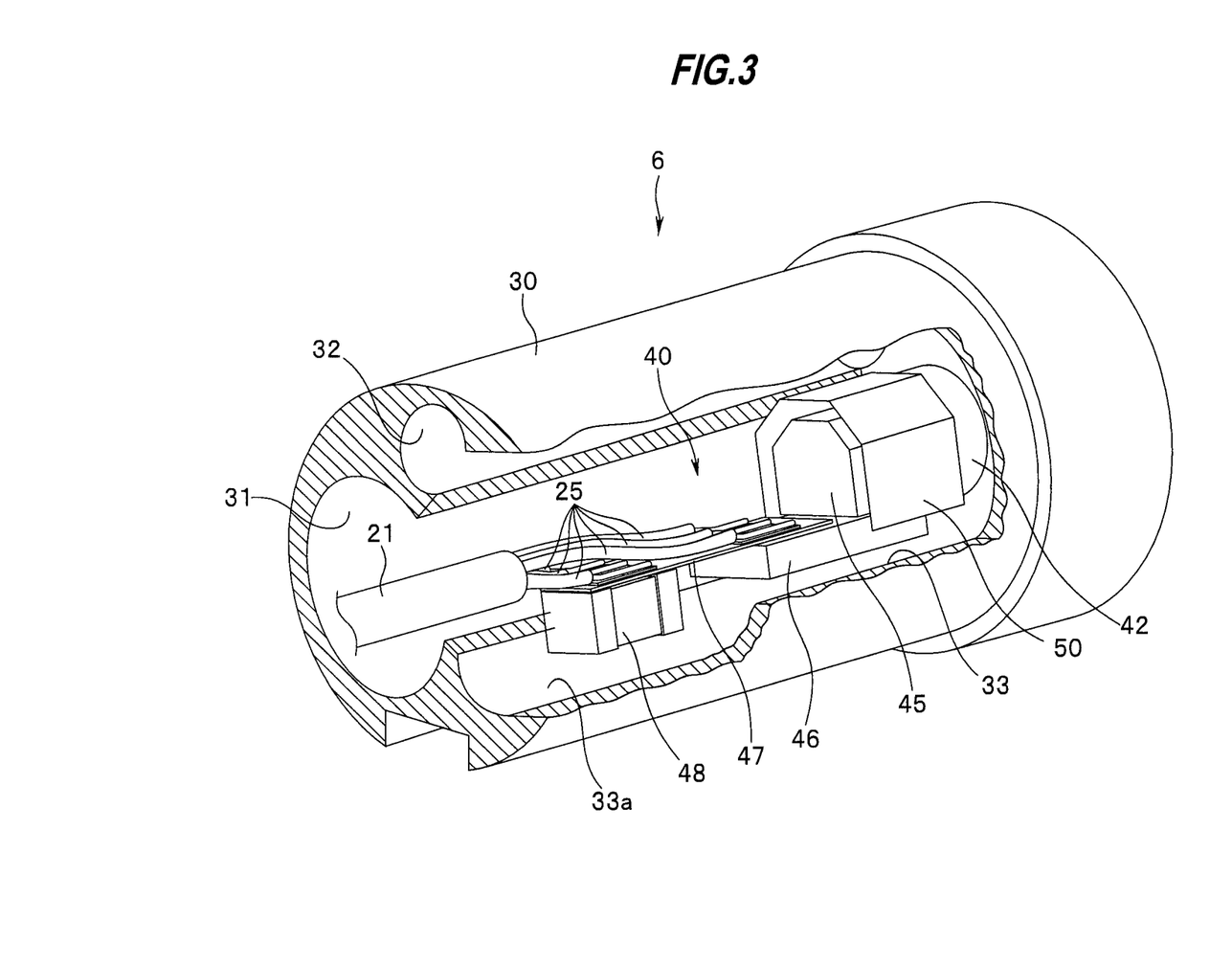
FIG. 3 relates to the first embodiment of the present invention, and is a perspective view showing the inner portion of the distal end portion in which an image pickup unit is placed.
Figure 4:
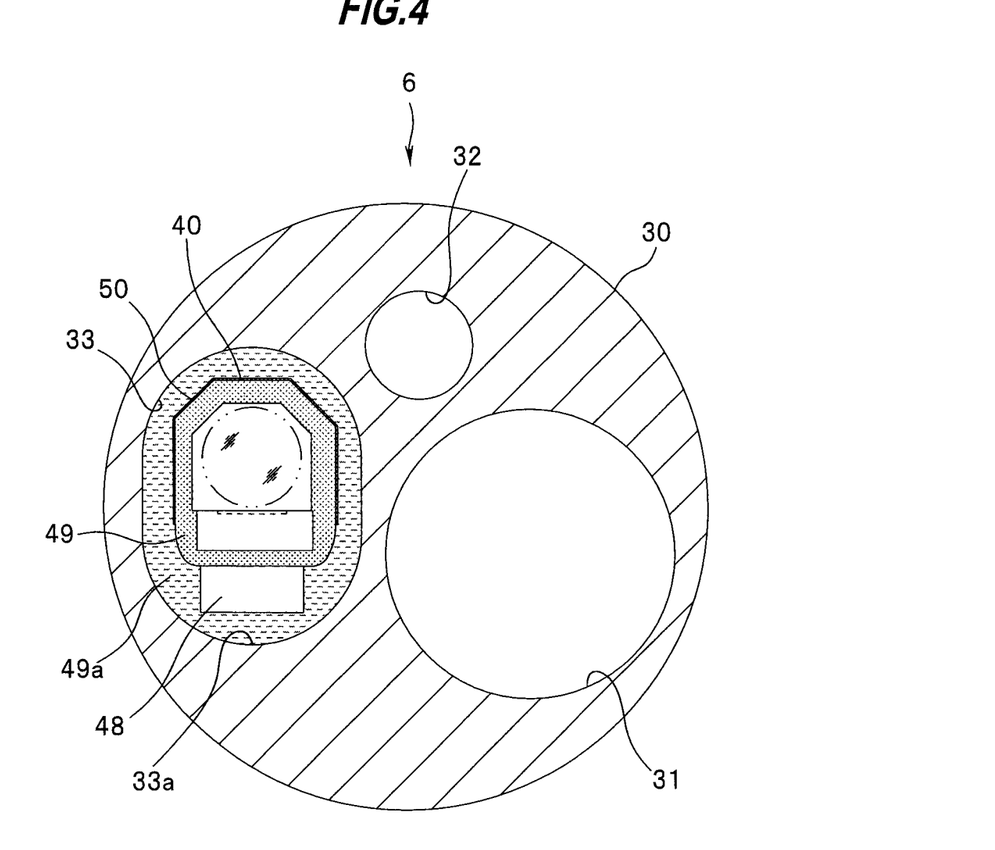
FIG. 4 relates to the first embodiment of the present invention, and is a sectional view of the distal end portion in which the image pickup unit is placed.
Figure 5:
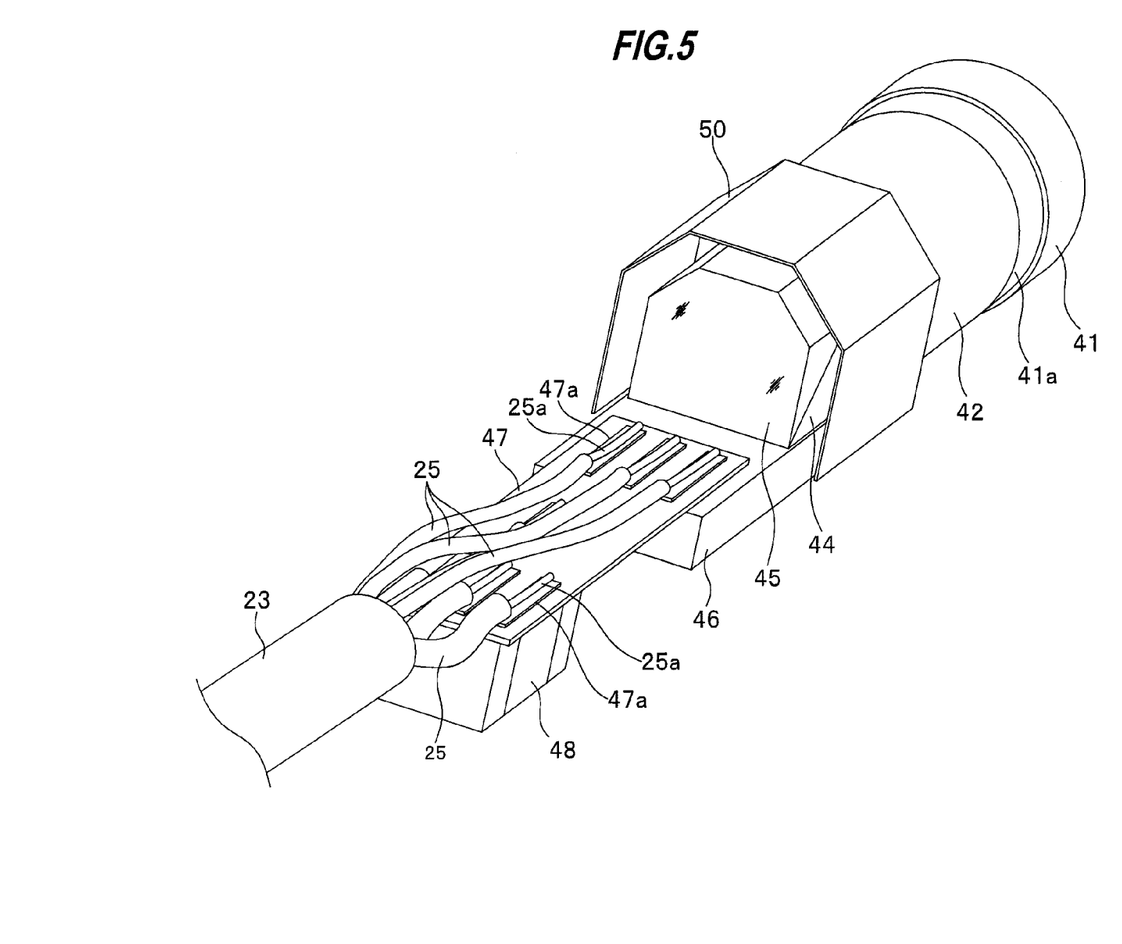
FIG. 5 relates to the first embodiment of the present invention, and is a perspective view showing a configuration of the image pickup unit.
Figure 6:
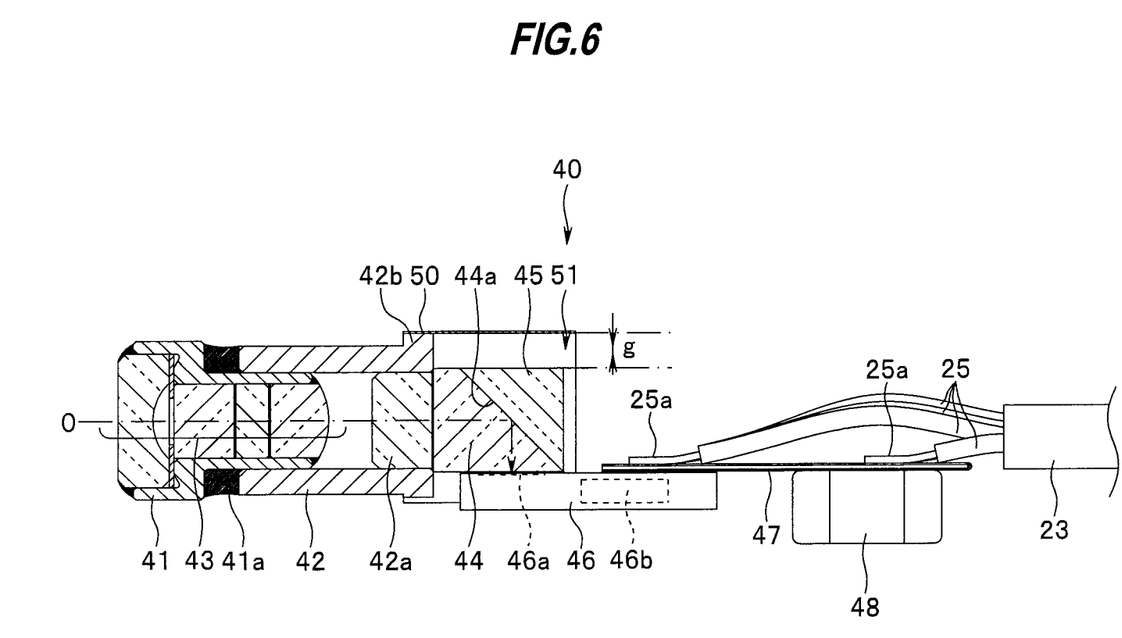
FIG. 6 relates to the first embodiment of the present invention, and is a partial cross-sectional view showing the image pickup unit from a side.
Figure 7:
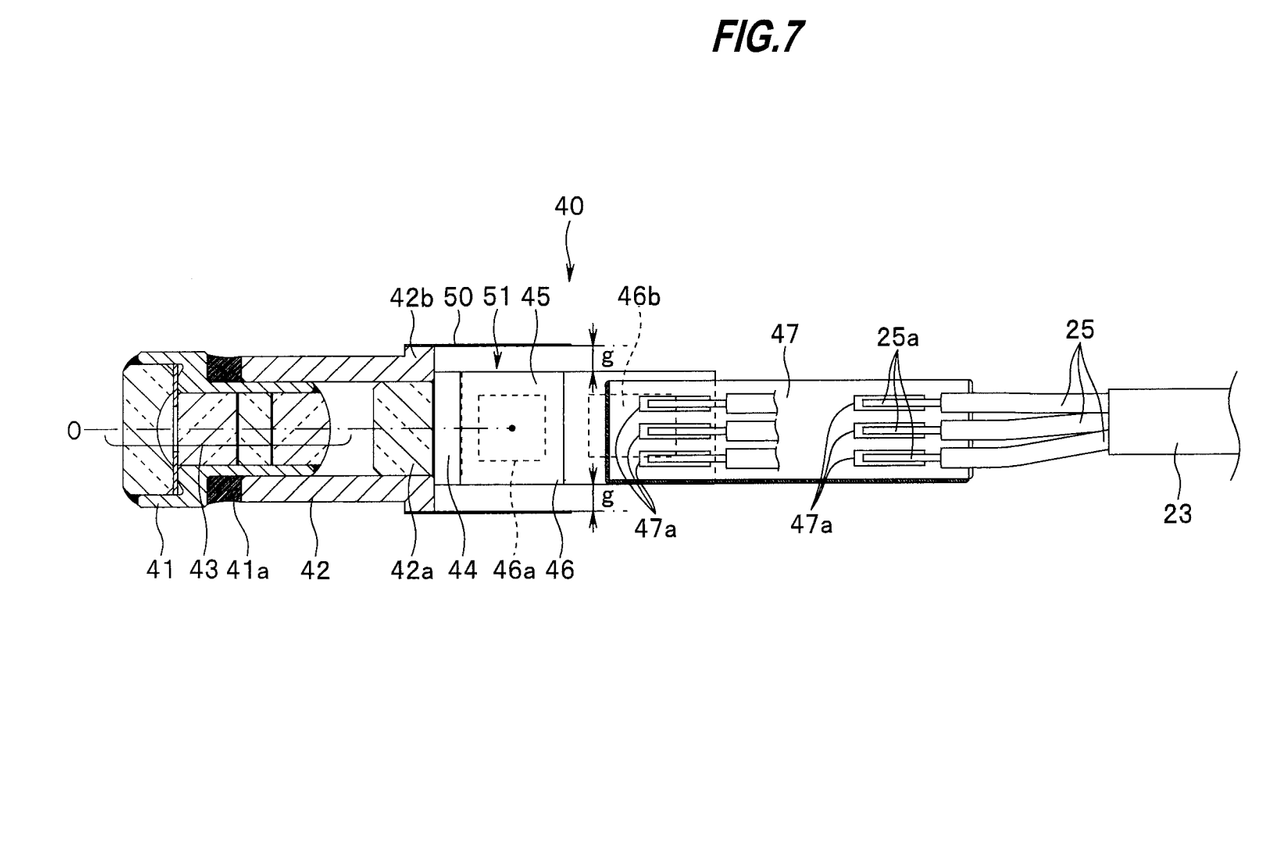
FIG. 7 relates to the first embodiment of the present invention, and is a partial cross-sectional view showing the image pickup unit from above.
Figure 8:
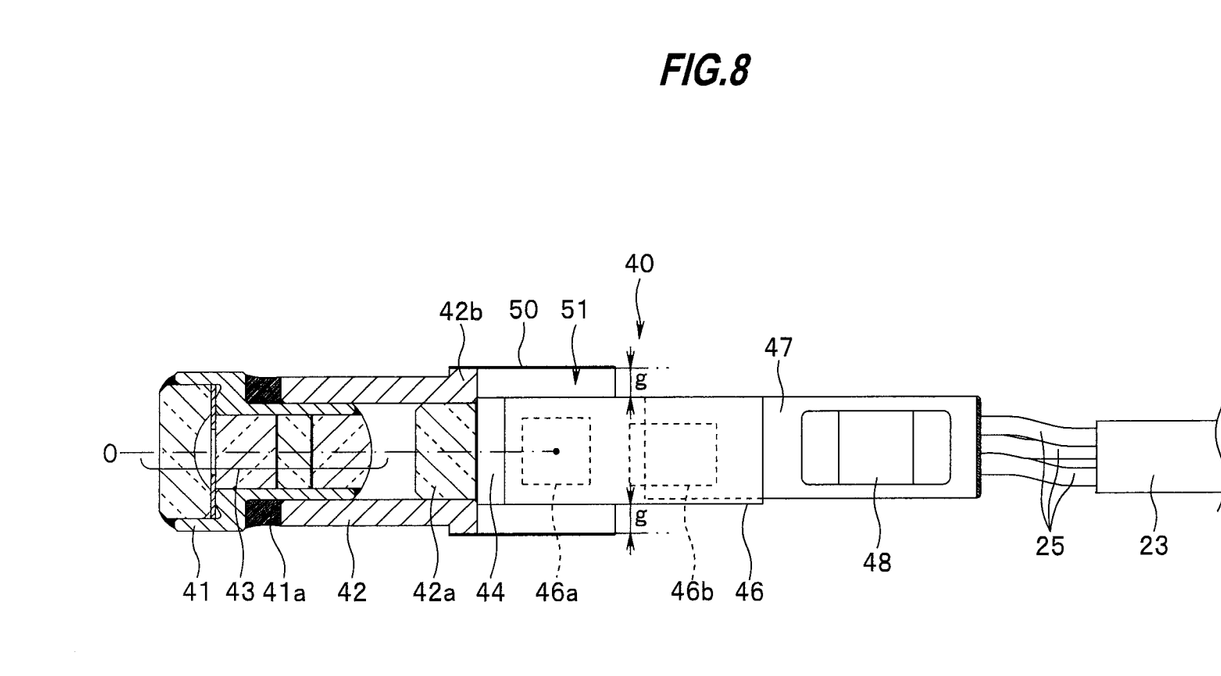
FIG. 8 relates to the first embodiment of the present invention, and is a partial cross-sectional view showing the image pickup unit from below.

First of all, a first embodiment of the present invention will be described hereinafter based on FIG. 1 to FIG. 10. FIG. 1 to FIG. 10 relate to the first embodiment of the present invention. FIG. 1 is a view showing an electronic endoscope system including an electronic endoscope apparatus. FIG. 2 is a perspective view showing an inner portion of a distal end portion of an insertion portion. FIG. 3 is a perspective view showing the inner portion of the distal end portion in which an image pickup unit is placed. FIG. 4 is a sectional view of the distal end portion in which the image pickup unit is placed. FIG. 5 is a perspective view showing a configuration of the image pickup unit. FIG. 6 is a sectional view showing the configuration of the image pickup unit. FIG. 7 is a top view showing the configuration of the image pickup unit. FIG. 8 is a bottom view showing the configuration of the image pickup unit.

As shown in FIG. 1, an electronic endoscope system 1 of the present embodiment is mainly configured by an electronic endoscope apparatus 2, a light source apparatus 3, a video processor 4, and a monitor 5.

The electronic endoscope apparatus 2 is configured by having a long and elongated insertion portion 9, an operation portion 10, and a universal cable 17 which is a composite cable in which an electric cable, and a light guide bundle for illuminating light transmission are inserted through an inner portion thereof. The insertion portion 9 of the electronic endoscope apparatus 2 is configured by having a distal end portion 6, a bending portion 7 and a flexible tube portion 8 in sequence from a distal end.

Further, the operation portion 10 is connected to one end of the flexible tube portion 8 of the insertion portion 9, and is configured by having a rear port portion 11 which is a bend preventing portion, a treatment instrument channel insertion portion 12 which is an opening of a treatment instrument channel through which various treatment instruments placed in the insertion portion 9 are inserted, and an operation portion body 13.

In the operation portion body 13, a bending operation knob 16 for performing bending operation of the bending portion 7 of the insertion portion 9 is pivotably placed, and switches and the like of various endoscope functions are provided. At the bending operation knob 16, a UD bending operation knob 14 for performing bending operation of the bending portion 7 in a vertical direction, and an RL bending operation knob 15 for performing bending operation of the bending portion 7 in a lateral direction are placed to be superimposed on each other.

The universal cable 17 which is extended from the operation portion 10 has an endoscope connector 18 which is detachable from the light source apparatus 3, at an extension end. The electronic endoscope apparatus 2 of the present embodiment transmits an illuminating light from the light source apparatus 3 to the distal end portion 6 by the light guide bundle not illustrated here. At the endoscope connector 18, a coil-shaped coil cable 19 is extended, and an electric connector 19a which is detachable from the video processor 4 is provided at an extension end of the coil cable 19.

The video processor 4 is electrically connected to the monitor 5 which displays an endoscopic image, performs signal processing of an electric signal photoelectrically converted by an image pickup unit for an endoscope (hereinafter, simply described as an image pickup unit) 20 described later of the electronic endoscope apparatus 2, and outputs the electric signal to the monitor 5 as an image signal.

In the inner portion of the bending portion 7 of the insertion portion 9 of the electronic endoscope apparatus 2, a plurality of substantially ring-shaped metal bending pieces 20a, 20b and 20c that are adjacent to one another and pivotably coupled to one another are provided as shown in FIG. 2. Further, at the distal end portion 6, the bending piece 20a at the most distal end is fixed, and a distal end rigid portion (also described as a distal end component portion) 30 which is a distal end frame made of metal and has a substantially columnar outer shape in this case is placed. Outer circumferential portions of a plurality of bending pieces 20a, 20b and 20c and the distal end rigid portion 30 are covered with a bending rubber not illustrated here.

In the distal end rigid portion 30, and the respective bending pieces 20a, 20b and 20c, a treatment instrument channel 21, a light guide bundle 22, various kinds of electric cables 23 and the like which are inserted through the inside of the insertion portion 9 are placed.

As shown in FIG. 3, in the distal end rigid portion 30, hole portions 31 and 32 in which the treatment instrument channel 21 and the light guide bundle 22 are individually inserted through and fixed via metal holding tubes and the like not illustrated, and a space portion 33 in which an image pickup unit 40 is disposed are formed. The hole portions 31 and 32 and the space portion 33 are formed from a distal end of the distal end rigid portion 30 to a proximal end thereof, and openings are formed in a distal end face and a proximal end face of the distal end rigid portion 30.

Next, a specific configuration of the image pickup unit 40 of the present embodiment will be described based on FIG. 4 to FIG. 8.

As shown in FIG. 5 to FIG. 8, the image pickup unit 40 is mainly configured by having a lens holding frame 41 which is one of optical system holding frames each in a quasi-cylindrical shape formed from a metal or the like, a prism holding frame 42 which is one of the optical system holding frames each in a quasi-cylindrical shape formed from a metal or the like, an optical lens group 43 which is an objective optical system, a prism 44 which reflects a luminous flux of an incident optical image to perform optical path conversion, a protection member 45 which is a highly thermal conductive member and a heat radiating member, an image sensor 46 which is image pickup means, is an element in a bare state in this case, and is a solid image pickup device such as a CCD and CMOS, an FPC (flexible print board) or TAB (Tape Automated Bonding) 47, and an electronic component 48.

The lens holding frame 41 is placed at a most distal end in the image pickup unit 40, and holds the optical lens group 43 in the inner portion, which condenses the incident luminous flux of an optical image of a subject. A distal portion of the prism holding frame 42 is fitted over a proximal end portion of the lens holding frame 41, and the lens holding frame 41 and the prism holding frame 42 are affixed to each other by an adhesive 41a. Further, a cover glass 42a which is adhered to a distal end face of the prism 44 by an optical adhesive is fixedly inserted and fitted into a proximal end portion of the prism holding frame 42. An optical system holding frame in which the lens holding frame 41 and the prism holding frame 42 are integrally formed may be adopted.

In the prism 44, a reflection surface 44a refracts the luminous flux of an optical image shown by an optical axis O in the drawings, which is incident from a distal end face side through the optical lens group 43, by substantially 90° and reflects the luminous flux to a bottom surface. The protection member 45 with a block body which is adhered by an adhesive is affixed to a surface side of the reflection surface 44a of the prism 44 in order to protect a reflective film of the reflection surface 44a. In the present embodiment, a dioptric system is configured by the prism 44 to which the protection member 45 is affixed.

The image sensor 46 is joined to a joining surface which is a bottom surface of the prism 44 by an optical adhesive, and a light receiving element 46a is placed on an opposed surface portion to the bottom surface of the prism 44, which is a top surface portion. Further, the image sensor 46 is provided with an electronic circuit portion 46b which includes an amplifier such as a transistor, in the inner portion of a middle of a proximal end side, and is a substantially plate-shaped image pickup package in which the electronic circuit portion 46b is packaged with the light receiving element 46a. A distal end portion of the FPC or TAB 47 is electrically connected to the top surface portion of the proximal end side of the image sensor 46.

The FPC or TAB 47 is extended to a rear from the image sensor 46, and has a plurality of connection lands 47a (see FIG. 5 and FIG. 7) on a top surface portion of a proximal end portion. Further, the FPC or TAB 47 is provided with the electronic component 48 on a bottom surface portion of the proximal end portion. A core wire 25a of a cable 25 is electrically connected to each of the connection lands 47a and the electronic component 48 by soldering or the like. The aforementioned electric cable 23 is made by a plurality of cables 25 being bundled and covered with an outer sheath.

Further, the image pickup unit 40 is coated with an adhesive for reinforcing in the periphery after each component is assembled thereto, and is modularized in a state in which an adhesive layer 49 (see FIG. 4) is formed. Thereafter, in the image pickup unit 40, the lens holding frame 41 is fitted in and fixed to the distal end rigid portion 30 with screws, and is disposed inside the space portion 33 of the distal end rigid portion 30. Thereafter, the adhesive 49a (see FIG. 4) is filled in a gap from the distal end rigid portion 30 which forms the space portion 33, and the image pickup unit 40 is affixed inside of the distal end rigid portion 30. In some of the drawings, the adhesive layer 49 and the adhesive 49a are not illustrated.

Further, in the space portion 33 in the distal end portion 6 in which the image pickup unit 40 is disposed, a recessed portion 33a is formed in an outside diameter direction so that the space portion 33 does not abut on the electronic component 48 which is placed on the bottom surface of the proximal end side of the FPC or TAB 47 (see FIG. 3 and FIG. 4).

Incidentally, on the light receiving element 46a of the image sensor 46, a photographing light shown by the optical axis O which is refracted by the reflection surface 44a of the prism 44 is incident to form an image. The light receiving element 46a generates electric charge corresponding to the brightness of the incident light, and performs photoelectric conversion.

In the image pickup unit 40 of the present embodiment which is configured as above, a light shielding member 50 is provided around top portions and side portions of the prism 44 and the protection member 45. The light shielding member 50 is placed apart from the prism 44, the protection member 45 and the image sensor 46 by a predetermined distance, as will be described later.

Here, a configuration of the light shielding member 50 of the present embodiment will be described in detail below.

Figure 9:
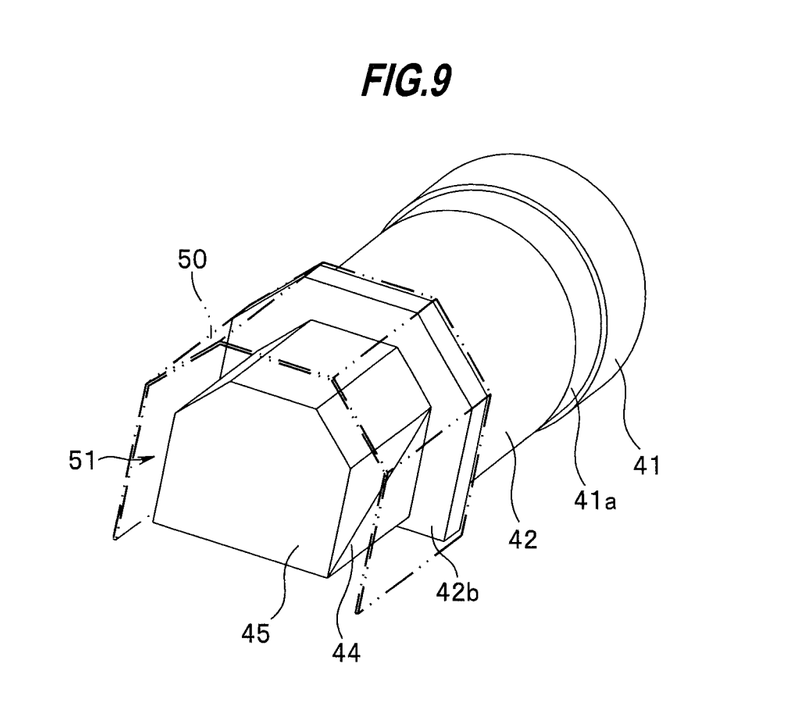
FIG. 9 relates to the first embodiment of the present invention, and is a perspective view for explaining joining of a prism holding frame and a light shielding member.

The light shielding member 50 is formed from a thin film metal such as nickel, and as shown in FIG. 9, is folded at four spots parallel along a longitudinal axis direction of the image pickup unit 40, and a distal end inner peripheral surface is joined so as to be in surface contact with five surfaces which are a top surface, both side surfaces and two slant surfaces formed by both side corner portions at a top portion side being cut out of, a joining portion 42b (see FIG. 9) hexagonal in section which is integrally formed at a proximal end portion of the prism holding frame 42, without a gap. The joining portion 42b in this case becomes a distal end light shielding surface which shields an unnecessary light (harmful light) other than the photographing optical image which is incident on the prism 44 from a front side, because the light shielding member 50 is joined to the joining portion 42b in surface contact therewith out a gap.

Figure 10:
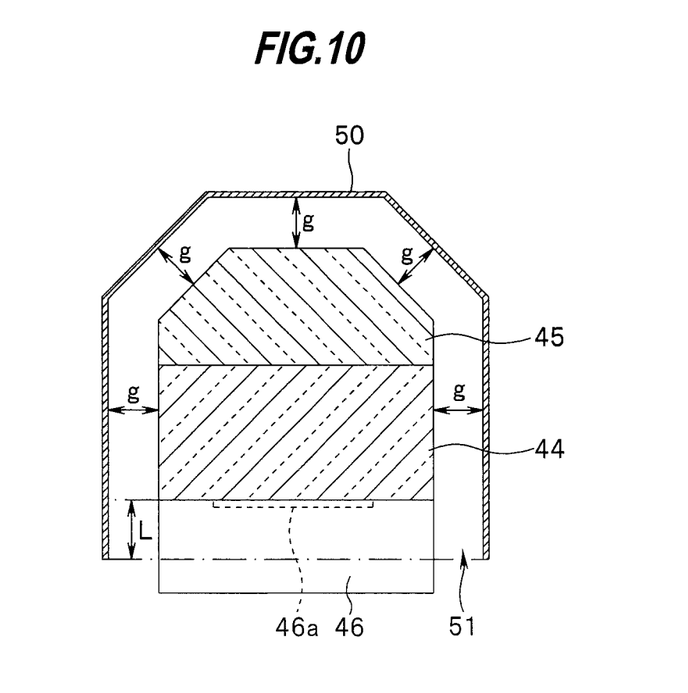
FIG. 10 relates to the first embodiment of the present invention, and is a sectional view of the image pickup unit in a position where the light shielding member is provided.

Further, as shown in FIG. 9 and FIG. 10, in the light shielding member 50, an air gap 51 is placed so as to be apart from the image sensor 46 by a predetermined distance. The light shielding member 50 is placed so that inner surfaces which form the air gap 51 by being opposed to the top surface, both the side surfaces and the two slant surfaces formed by both the side corner portions at the top portion side being cut out which are around the longitudinal direction, except for the bottom surfaces of the prism 44 on which the image sensor 46 is joined and the protection member 45, become parallel with the surfaces respectively apart therefrom by a constant distance g.

More specifically, the top surface, both the side surfaces and the two slant surfaces of the joining portion 42b of the prism holding frame 42 to which the light shielding member 50 is joined become the surfaces which are located outward by the constant distance g respectively from the top surfaces, both the side surfaces and the two slant surfaces of the prism 44 held by the prism holding frame 42 and the protection member 45. The distal end inner surfaces of the light shielding member 50 are joined to the top surface, both the side surfaces and the two slant surfaces of the joining portion 42b, and the air gap 51 is formed so that the inner surfaces of the light shielding member 50 are opposed to and apart from the prism 44 and the protection member 45 at the constant distance g.

The light shielding member 50 is extended to positions where the light shielding member 50 is superimposed on both side surfaces of the image sensor 46 to cover the inside of the same surface as the light receiving surface (element surface) of the light receiving element 46a of the image sensor 46. More specifically, in the light shielding member 50, both the side surface portions each have a predetermined length L downward from the light receiving surface of the light receiving element 46*a*, and each of both the side surface portions is extended to the position where each of the side surface portions is superimposed on the opposed side surface of the image sensor 46.

The metallic light shielding member 50 is placed by the air gap 51 being formed so as to be apart from the image sensor 46 by the predetermined distance without contacting the image sensor 46 in a bare state having electric charge, whereby the image pickup unit 40 of the present embodiment which is configured as above has the structure which prevents the possibility of electrostatic destruction of the image sensor 46.

The image pickup unit 40 is configured to shield unnecessary lights (harmful lights) other than the photographing optical images incident on the prism 44, by the light shielding member 50 which is disposed to be opposed to the surfaces around the longitudinal direction of the prism 44 and the protection member 45 except for the surfaces to which the image sensor 46 is joined.

The light shielding member 50 shields a harmful light such as a scattered light by the illuminating light guided by the light guide bundle 22, and prevents the harmful light from being incident on the light receiving element 46*a* of the image sensor 46 from the periphery of the prism 44 and the protection member 45, for example, when a gap due to an assembly error of the distal end rigid portion 30 which is the distal end frame is formed, or the distal end rigid portion 30 is formed by a transparent resin member to achieve weight reduction. Therefore, the image pickup unit 40 of the present embodiment can acquire a favorable video.

Further, the image pickup unit 40 can be formed into a film shape with an extremely thin thickness, while securing necessary rigidity and also can be prevented from being upsized, by using a metal for the light shielding member 50.

Furthermore, in the image pickup unit 40, the separation distance g of the air gap 51 which is formed by the respective inner surfaces of the light shielding member 50 and the surfaces around the longitudinal direction of the prism 44 and the protection member 45 being opposed to each other is made the same, whereby the thickness of the adhesive layer 49 (see FIG. 4) which is filled in the air gap 51 becomes uniform, and therefore, stress due to shrinkage on curing, thermal expansion and the like of the adhesive layer 49 becomes uniform. Therefore, the joining surfaces of the light shielding member 50, and the prism 44 and the protection member 45 become difficult to peel off.

As described above, the image pickup unit 40 of the present embodiment is structured to prevent upsizing and prevent the possibility of electrostatic destruction of the image sensor 46, and is configured to be able to acquire a favorable video by being provided with the light shielding member 50 which shields an unnecessary light to the light receiving element 46*a* of the image sensor 46.

Second Embodiment

Next, an image pickup unit of a second embodiment will be described below based on FIG. 11 and FIG. 12.

Figure 11A:
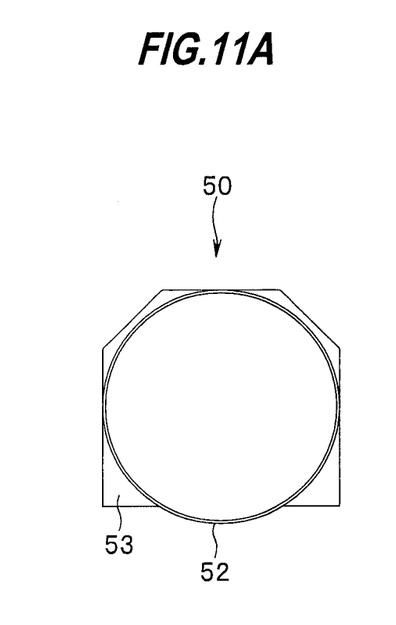
FIG. 11A shows a configuration of a light shielding member according to a second embodiment of the present invention, and is a front view of the light shielding member.
Figure 11B:
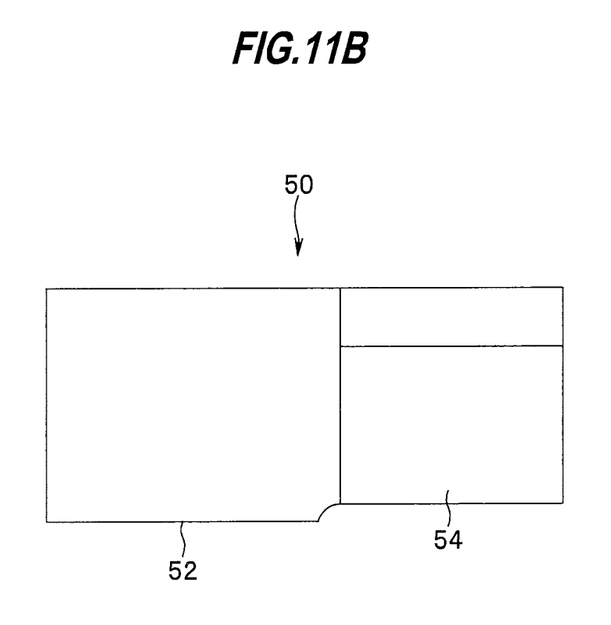
FIG. 11B shows the configuration of the light shielding member according to the second embodiment of the present invention, and is a side view of the light shielding member.
Figure 11C:
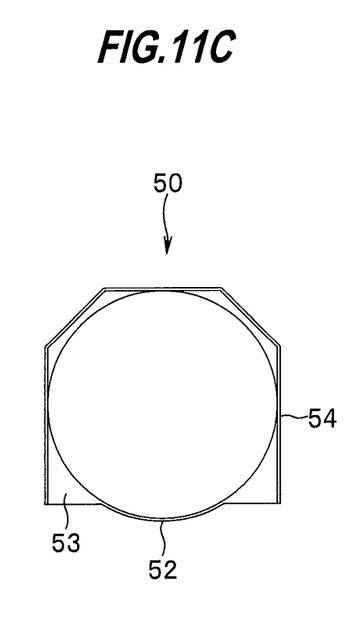
FIG. 11C shows the configuration of the light shielding member according to the second embodiment of the present invention, and is a rear view of the light shielding member.
Figure 12:
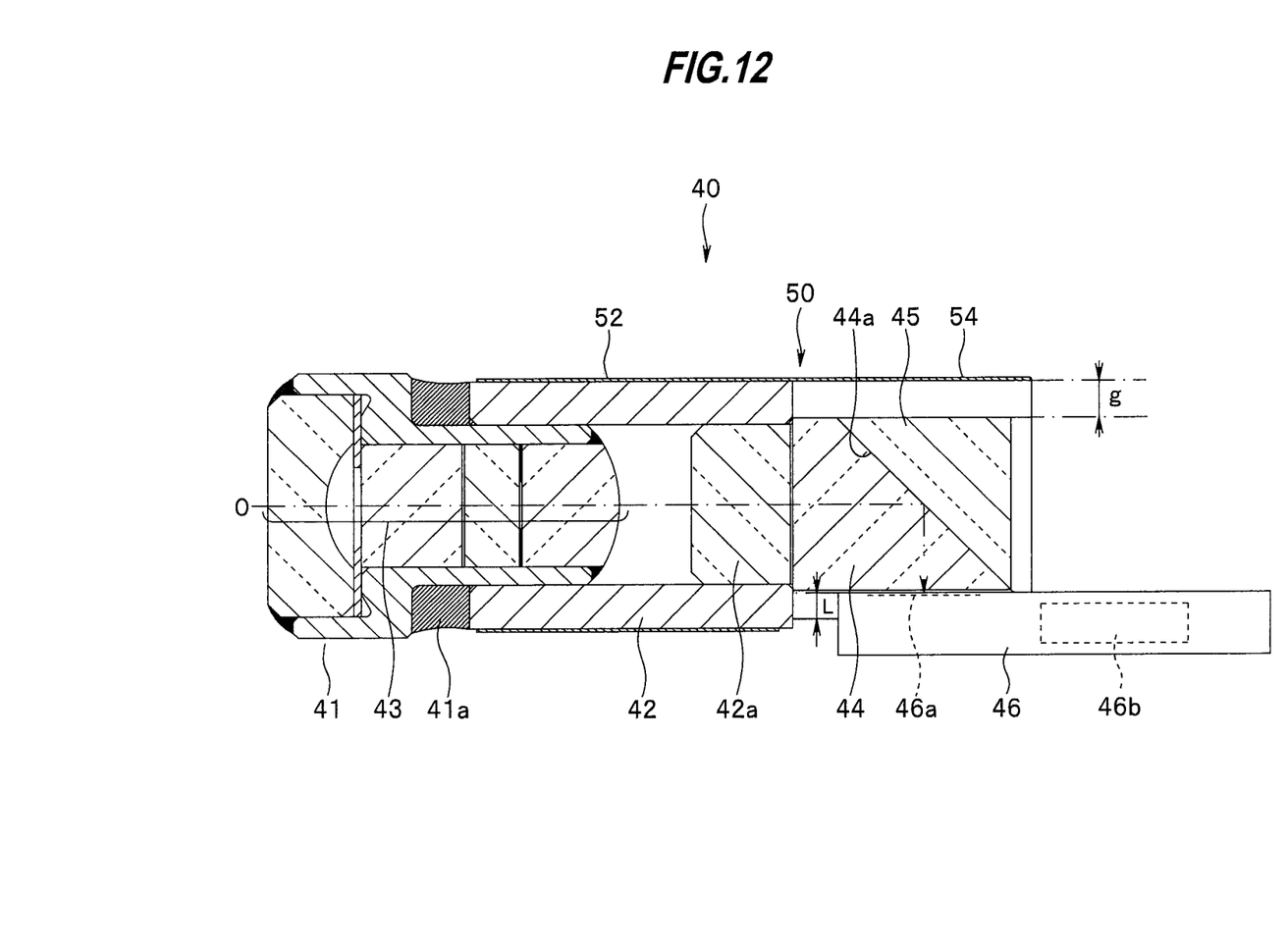
FIG. 12 shows the configuration of the light shielding member according to the second embodiment of the present invention, and is a sectional view showing a state in which the light shielding member is fitted in a prism holding frame.

FIG. 11 and FIG. 12 relate to the second embodiment of the present invention. FIG. 11 shows a configuration of a light shielding member. FIG. 11A is a front view of the light shielding member. FIG. 11B is a side view of the light shielding member. FIG. 11C is a rear view of the light shielding member. FIG. 12 is a sectional view showing a state in which the light shielding member is fitted in a prism holding frame. Further, in the following description, for the same components as those of the first embodiment, the same reference signs are used for the convenience of explanation, and the detailed description and the operational effects of the components will be omitted.

As shown in FIG. 11, the light shielding member 50 which is provided in the image pickup unit 40 of the present embodiment is also formed from a metal in this case, and is configured by having a holding portion 52 in a cylindrical shape, a distal end light shielding portion 53 which is integrally coupled to the holding portion 52 and configures a bridge portion, and a light shielding portion 54 which is integrally coupled to the distal end light shielding portion 53 and is folded at four spots parallel along a longitudinal axis direction, in sequence from a distal end side.

The holding portion 52 is slipped over and fitted on the prism holding frame 42 as shown in FIG. 12. The prism holding frame 42 in this case is configured not to be provided with the joining portion 42*b* (see FIG. 9) described in the first embodiment.

The distal end light shielding portion 53 becomes a distal end light shielding surface which shields an unnecessary light (harmful light) other than a photographing optical image which is incident on the prism 44 from a front side in this case, in place of the above described joining portion 42*b* described in the first embodiment. The distal end light shielding portion 53 is formed so that the holding portion 52 and the light shielding portion 54 are integrally linked to each other without a gap.

A configuration of the light shielding portion 54 is the same configuration as the light shielding member 50 described in the first embodiment which does not include the holding portion 52 and the distal end light shielding portion 53, and therefore, the detailed description thereof will be omitted.

The image pickup unit 40 of the present embodiment which is configured as above is provided with the holding portion 52 in the cylindrical shape in the light shielding member 50, whereby assembly of the light shielding member 50 to the prism holding frame 42 is facilitated, and the assemblability can be improved, in addition to the effect of the first embodiment. Further, the light shielding member 50 is integrally provided with the distal end light shielding portion 53, whereby the distal end light shielding portion 53 becomes a reinforcing member, the rigidity is improved, and in particular, deformation of the light shielding portion 54 is prevented.

In the present embodiment, the light shielding member 50 including the holding portion 52 which is slipped over and fitted on the prism holding frame 42 is shown, but the prism holding frame 42 and the light shielding member 50 may be integrally formed, as a matter of course.

Third Embodiment

Next, an image pickup unit of a third embodiment will be described below based on FIG. 13.

Figure 13:
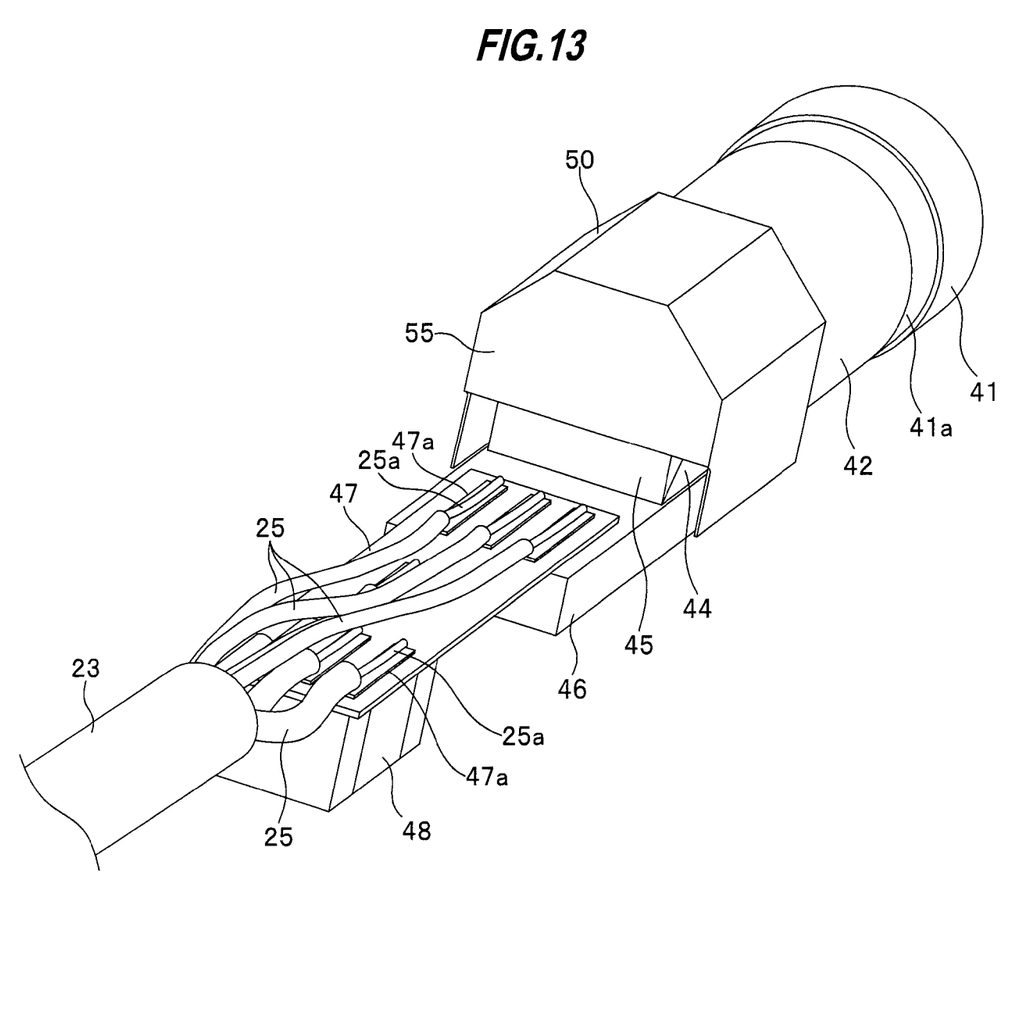
FIG. 13 is a perspective view of a configuration of an image pickup unit according to a third embodiment of the present invention.

FIG. 13 relates to a third embodiment of the present invention, and is a perspective view showing a configuration of the image pickup unit. Further, in the following description, for the same components as those of the first embodiment, the same reference signs are used for the convenience of explanation, and the detailed description and the operational effects of the components will be omitted.

As shown in FIG. 13, in the light shielding member 50 of the image pickup unit 40 of the present embodiment, a proximal end light shielding portion 55 which is a proximal end light shielding surface which shields an unnecessary light (harmful light) other than a photographing optical image which is incident on the prism 44 from a rear side is integrally formed. The proximal end light shielding portion 55 is formed in a position at an opposite side from an incident side of the luminous flux of an optical image to the prism 44 to be opposed to and apart from a proximal end surface of the protection member 45 by a predetermined distance.

Further, in the proximal end light shielding portion 55, a separation distance of an air gap which is formed by being opposed to the proximal end surface of the protection member 45 is desirably made the same as the distance g (see FIG. 10) described in the first embodiment. Further, the proximal end light shielding portion 55 is placed apart from the image sensor 46 by a predetermined distance as a matter of course.

By being configured as above, the image pickup unit 40 of the present embodiment also can shield an unnecessary light (harmful light) other than the photographing optical image incident on the prism 44 from the rear side, by the proximal end light shielding portion 55, and is configured to be able to acquire a more favorable video, in addition to the effect of the first embodiment. Further, the light shielding member 50 is integrally provided with the proximal end light shielding portion 55, whereby the proximal end light shielding portion 55 becomes a reinforcing member, improves the rigidity and prevents deformation of the light shielding portion 54 in particular.

The proximal end light shielding portion 55 of the present embodiment may be provided in the light shielding member 50 of the second embodiment as a matter of course.

The invention described above is not limited to the above described respective embodiments, and other than the embodiments, various modifications can be carried out within the range without departing from the gist of the invention in the stage of carrying out the invention. Further, each of the embodiments includes the invention at various stages, and various inventions can be extracted by appropriate combinations in the plurality of components which are disclosed.

For example, even if several components are deleted from all the components shown in each of the embodiments, the configuration from which the components are deleted can be extracted as the invention, as long as the effect described can be obtained, with respect to the problems to be solved by the invention.

What is claimed is:

1. An image pickup unit for an endoscope, comprising:
   a prism that reflects a luminous flux of an optical image incident on an optical lens group and performs optical path conversion;
   an image sensor in a bare state that is joined to the prism, and includes a light receiving element on which the luminous flux is incident and forms the optical image; and
   a light shielding member that is placed to be opposed to and cover at least surfaces of the prism around an optical axis of the optical lens group, except for a joining surface of the prism to the image sensor so that an air gap apart from the image sensor by a predetermined distance is provided, shields incidence of a harmful light onto the light receiving element, and is formed from a metal thin film,
   wherein the light shielding member covers an inside of a same surface as a light receiving surface of the light receiving element and is provided to extend to a position where the light shielding member is superimposed on both side surfaces of the image sensor by a predetermined length with respect to the light receiving surface, the light shielding member being opposed to at least the surfaces of the prism around the optical axis of the optical lens group except for the joining surface of the prism to the image sensor to be apart therefrom with a first separation distance, and extended to a position where the light shielding member is superimposed on the both side surfaces of the image sensor by a second separation distance.

2. The image pickup unit for an endoscope according to claim 1, further comprising:
   an optical system holding frame that holds the optical lens group, or the prism,
   wherein the light shielding member is joined to the optical system holding frame.

3. The image pickup unit for an endoscope according to claim 2, wherein in the light shielding member, a holding portion which is fitted in the optical system holding frame is integrally formed.

4. The image pickup unit for an endoscope according to claim 1, further comprising:
   an optical system holding frame that holds the optical lens group, or the prism,
   wherein the light shielding member is formed integrally with the optical system holding frame.

5. The image pickup unit for an endoscope according to claim 1, wherein an adhesive layer filled with an adhesive is formed in the air gap.

6. The image pickup unit for an endoscope according to claim 5, wherein in the light shielding member, the predetermined distance is constant so that a thickness of the adhesive layer becomes uniform.

7. The image pickup unit for an endoscope according to claim 1, wherein the light shielding member has a proximal end light shielding portion which is formed in a position at an opposite side from an incident side of the luminous flux to the prism, and shields incidence of a harmful light from a rear of the light receiving element.

8. The image pickup unit for an endoscope according to claim 2, wherein the light shielding member, or the optical system holding frame has a distal end light shielding portion which is formed in a position at an incident side of the luminous flux to the prism, and shields incidence of a harmful light from a front of the light receiving element.

9. The image pickup unit for an endoscope according to claim 1, wherein the first separation distance and the second separation distance are equal to each other.

* * * * *